United States Patent [19]

Lucero

[11] Patent Number: 5,504,113
[45] Date of Patent: Apr. 2, 1996

[54] ENHANCEMENT OF BENZALKONIUM CHLORIDE PRESERVATIVE ACTIVITY IN FORMULATIONS CONTAINING AN INCOMPATIBLE DRUG

[75] Inventor: Jasmin C. Lucero, Irvine, Calif.

[73] Assignee: Allergan, Inc., Irvine, Calif.

[21] Appl. No.: 204,853

[22] Filed: Mar. 2, 1994

[51] Int. Cl.$^6$ .......................... A61K 31/205; A61K 31/14
[52] U.S. Cl. ........................... 514/554; 514/643; 514/912
[58] Field of Search ................................ 514/554, 643, 514/912

[56] References Cited

PUBLICATIONS

Chemical Abstracts, 110:219120 (1989). Fu et al.

Primary Examiner—Zohreh Fay
Attorney, Agent, or Firm—Walter A. Hackler

[57] ABSTRACT

A formulation and method includes an acceptable drug, such as Prostaglandins, Flurbiprofen, Keterolac Tromethamine, Cetirizine HCl Indomethacin and Bufrolin, which are interactive with benzalkonium chloride to form a precipitate along with benzalkonium chloride acting as a preservative and an amino acid having enough positive charge at the pH of the formulation and/or Tromethamine present in an amount sufficient to interfere with the interaction between the drug and benzalkonium chloride in order to maintain the preservative activity of the benzalkonium chloride. Further, the use of Lysine, L-arginine, or Histidine is also useful in reducing the cytotoxicity of the formulation.

23 Claims, 1 Drawing Sheet

ENHANCEMENT OF BENZALKONIUM CHLORIDE PRESERVATIVE ACTIVITY IN FORMULATIONS CONTAINING AN INCOMPATIBLE DRUG

The present invention generally relates to improved formulations and solutions and more particularly to improved preservative systems for acceptable drug formulations which have an incompatibility with benzalkonium chloride (BAK) such as Prostaglandins, Flurbiprofen, Ketorolac Tromethamine, Cetirizine HCl and Indomethacin. More specifically, the present invention pertains to the preservative for an ophthalmologically acceptable drug such as Bufrolin having activity for treating seasonal allergies, allergic conjunctivitis, giant papillar conjunctivitis, and vernal keratoconjunctivitis.

Ophthalmologically acceptable drug formulations generally contain effective compounds and a number of ophthalmologically acceptable excipients. formulations generally include solutions, ointments, and suspensions, etc. The formulations may include excipients such as stabilizing agents, surfactants, buffering systems, chelating systems, viscosity agents, tonicity agents, and, importantly, a preservative.

Ophthalmic formulations, understandably, must be sterile and if a multi-dose regimen is intended, the formulation must be preserved with an effective antimicrobial agent.

As discussed in U.S. Pat. No. 5,110,493, organo-mercurials have been used extensively as the preservatives in ophthalmic solutions. As reported in this reference, these compounds pose difficulties due to potential mercury toxicity as well as poor chemical stability.

Therefore, benzalkonium chloride, which is a quaternary ammonium compound, has been widely used in ophthalmic solutions. It is also well-known however, that benzalkonium chloride is considered incompatible with annionic drugs, forming insoluble complexes which cause the solution to turn cloudy.

This is because of the fact that many annionic drug entities carry a negative charge at physiological pH. In fact, all acidic drug entities will carry a negative charge at all pH's above their pKa's.

In the case of benzalkonium chloride, which is a positively charged preservative, insoluble complexes can be formed with acidic drug entities causing the drug to precipitate out of solution. Concomitant with the removal of the drug from solution is the removal of benzalkonium chloride, thereby rendering this quaternary germicide incapable of performing its function as an antimicrobial agent.

Benzalkonium chloride is a mixture of alkylbenzyldimethylammonium chloride of the general formula as shown below in which R represents a mixture of the alkyls from $C_8H_{17}$ to $C_{18}H_{37}$

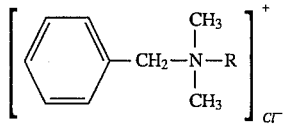

As hereinbefore noted, it is well-known that benzalkonium chloride is generally incompatible with anionic detergents or anionic drug compounds. See U.S. Pat. No. 5,110,493, and The Merck Index, 11th Edition, Merck & Co., Inc., 1989.

The present invention specifically relates to the discovery that an additive having a positive charge at the pH of the formulation can be used to compete with benzalkonium chloride and reduce complexation of any anionic drug with the benzalkonium chloride and thereby enhance the preservative effectiveness of the benzalkonium chloride.

SUMMARY OF THE INVENTION

A formulation in accordance with the present invention generally includes an acceptable drug which is interactive with benzalkonium chloride in combination with the very entity, benzalkonium chloride, with which the acceptable drug forms a complex, thereby removing the benzalkonium chloride from solution, and consequently reducing its effectiveness as a preservative. As noted, the benzalkonium chloride is added as a preservative and is active in that regard. Examples of such drugs include, but not limited to, Prostaglandins, Flurbiprofen, Keterolac Tromethamine, Cetirizine HCl Indomethacin and Bufrolin.

In combination with the acceptable drug and the benzalkonium chloride is an additive, having a net positive charge at the pH of the formulation, and present in amounts sufficient to enhance preservative effectiveness of the benzalkonium chloride. An effective amount is sufficient for the additive to compete with the benzalkonium chloride for the interaction of the ophthalmologically acceptable drug, thereby freeing more benzalkonium chloride and providing overall enhancement of the preservative activity of the benzalkonium chloride.

More particularly, an ophthalmologically acceptable drug may comprise bufrolin and the additive may comprise an amino acid having a net positive charge at the pH of the formulation present in sufficient amounts to interfere with the interaction between the drug and the benzalkonium chloride in order to maintain the preservative activity of the benzalkonium chloride.

More particularly, the amino acid may be selected from a group consisting essentially of Lysine, L-arginine and Histidine.

More specifically, the ophthalmic solution in accordance with the present invention includes bufrolin as the ophthalmologically acceptable drug and present in an amount of up to about 4% w/v. Preferably, the amino acid comprises L-arginine present in an amount between about 0.5% and about 5% w/v.

Utilization of the L-arginine reduces the amount of benzalkonium chloride necessary as a preservative and accordingly, in accordance with the present invention, the benzalkonium chloride may be present in an amount about 100 ppm or less.

As an alternative embodiment of the present invention, the additive comprises Tromethamine present in an amount of between about 0.3% and about 2% w/v.

In another embodiment of the present invention, a plurality of additives, each having a net positive charge at the pH of the formulation, are utilized in an amount sufficient to inhibit formation of an insoluble complex between the benzalkonium chloride and the ophthalmologically acceptable drug. More particularly, in this last-mentioned embodiment, the ophthalmologically acceptable drug formulation comprises both an amino acid having a net positive charge at the pH of the formulation and Tromethamine. The amino acid may comprise either Lysine, L-arginine, or Histidine, or combinations thereof, but preferably comprises L-arginine.

In addition, the utilization of L-arginine and Tromethamine together reduces the amount of BAK necessary as a preservative and accordingly, in accordance with the present invention, the BAK may be present in an amount about 100 ppm or less.

BRIEF DESCRIPTION OF THE DRAWINGS

The advantages and features of the present invention will be better understood by the following description when considered in conjunction with the accompanying drawing in which.

DETAILED DESCRIPTION

Figure 1:
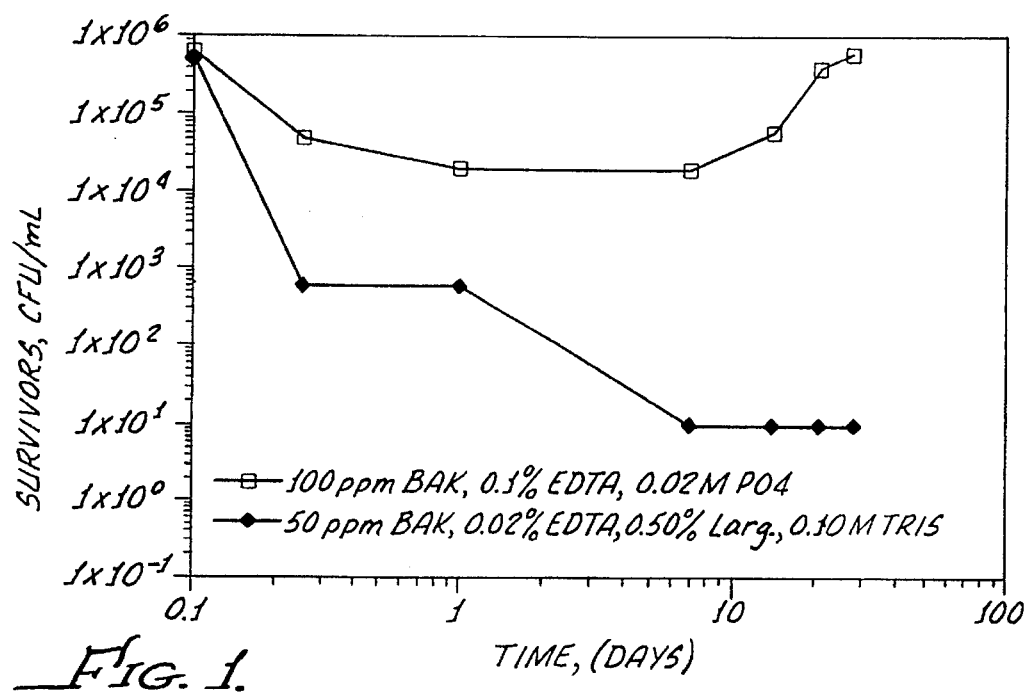
FIG. 1 is a comparison of bacterial (*P. aeruginosa*) recoveries of formulations with and without L-arginine and Tromethamine.

Bufrolin is a classic example of an anionic drug that forms an insoluble complex with benzalkonium chloride. Bufrolin is 6-n-Butyl, 1,4,7,10-tetrahydro-4,10-dioxo-1,7-phenanthroline-2,8-dicarboxylic acid. As hereinabove noted, this drug has activity for treating seasonal allergies, allergic conjunctivitis, giant papillar conjunctivitis and vernal keratoconjunctivitis. It is to be appreciated that while this particular drug is cited throughout here as an example, other anionic drugs that form an insoluble complex with benzalkonium chloride are to be considered to be within the scope of the present invention.

It is also well-known that benzalkonium chloride (BAK), alone or in combination with disodium edetate (EDTA), has been widely used for many years as an ophthalmic preservative. This preservative, through extensive testing and use, has been proven to be one of the most effective and rapid-acting preservatives which is stable over the pH range which most ophthalmic products are formulated.

It is also known that the addition of between about 0.01% and about 0.1% EDTA increases the effectiveness of BAK against some resistant strains of the pseudomonas species.

Unfortunately, since BAK is a cationic compound, incompatibility with anionic drugs limits its use as a preservative. The synergism expected from the combination of BAK and EDTA has not been successful in preserving formulations having high concentrations of anionic drugs such as Bufrolin which require up to 4 % w/v for the treatment of allergic conjunctivitis in phosphate-buffered solutions with a pH between about 6 and about 8, and preferably about 7.4.

Amino acids suitable for use in the present invention having a positive charge at the pH of the formulation may include Lysine, Arginine and Histidine, having positively charged R groups, as shown below with the amino and carboxyl group ionized as they would occur at pH 7.0. These amino acids can be used individually, or in combination with one another and Tromethamine or Tris [2-Amino-2-(hydroxymethyl)-1,3-propanediol], which is a well-known biological buffer.

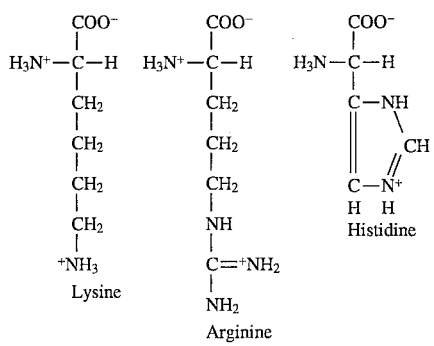

Microbiological studies assessing the preservative efficacy of the formulation made in accordance with the present invention, as well as cytotoxicity tests, have been performed in accordance with the following methods:

Preservative Efficacy Test

Materials:
a. Test Organisms
   *S. aureus, P. aeruginosa, E. coli, C. albicans, A. niger*
b. Recovery Media
   Trypticase soy broth with neutralizing phosphate buffer and Polysorbate 80
   Trypticase Soy Agar with 1.0% Glucose Method:
1. 10 mL aliquots of the test samples are inoculated with 50 µL of test organisms to yield a final concentration of about $5 \times 10^6$ CFU/mL.
2. The samples are tested for survivors on D-0, 6 hour, D-1, D-14, D-21, D-28.

Cytotoxicity—Inulin Permeability Assay $2 \times 10^5$ MDCK (Madin-Darby Canine Kidney) cells on collagen-coated semi-permeable inserts are incubated for 2 days prior to the assay. 0.4 µCi $^{14}$C-inulin is added to 400 µL of the test sample and 100 µL of this is placed in each insert. At each timepoint, 20 µL of sample is taken from outside of the insert and radioactivity measured using scintillation counting.

The preservative criteria for ophthalmic preparations utilized in the studies include British Pharmacopeia (BP-88), Deutsches Arzneibuch (DAB-9) and United States Pharmacopeia (USP) as shown in Table I.

TABLE I

| Preservative Criteria for Ophthalmic Preparations | | | |
|---|---|---|---|
| | BP-88 | DAB-9 | USP |
| S. aureus #6538P | −3 log in 6 hrs 0 in 24 hrs | −2 log in 24 hrs −3 log in 7 days | −3 log in 14 days |
| P. aeruginosa #9027 | −3 log in 6 hrs 0 in 24 hrs | −2 log in 24 hrs −3 log in 7 days | −3 log in 14 days |
| E. coli #8739 | N/A | N/A | −3 log in 14 days |
| C. albicans #10231 | −2 log in 7 days 0 incr. 28 days | −1 log in 14 days | 0 incr. in 14–28 days |
| A. niger #16404 | −2 log in 7 days 0 incr. 28 days | −1 log in 14 days | 0 incr. in 14–28 days |

Table II shows the preservative efficacy test results of some formulations:

TABLE II

| Preservative Efficacy Test Results of Formulations | | | |
|---|---|---|---|
| Preservative System | Buffer | DAB-9 | USP |
| 100 ppm BAK, 0.10% EDTA | 0.02 M PO$_4$ | fail | fail |
| 70 ppm BAK, 0.03% EDTA | 0.10 M Tris | pass | pass |
| 50 ppm BAK, 0.05% EDTA | 0.10 M Tris | fail | fail |
| 50 ppm BAK, 0.02% EDTA, 0.50% L-arginine | 0.10 M Tris | pass | pass |

Sample formulations utilizing L-arginine, Lysine or Histidine include:
Anionic drug—e.g. Bufrolin—4% w/v Cationic preservative—e.g. BAK Chelators—e.g. Na₂EDTA Buffers—e.g. tris, phosphate Salts—e.g. NaCl for tonicity adjustment Dilute acid/base—e.g. HCl/NaOH for pH adjustment As shown in Table II, the preservative efficacy test (PET) showed that, even with as much as 100 ppm BAK and 0.1% EDTA in 0.02M phosphate buffer (pH 7.4), the 4% w/v Bufrolin formulation failed to meet the USP criteria.

The use of Tris (Tromethamine) as a buffer and counterion enhanced the efficacy of the BAK/EDTA combination and a formulation of 4% w/v Bufrolin with 70 ppm BAK, 0.03% EDTA, and 0.1M Tris pass the DAB-9 test, which is a more stringent criterion than that of the USP.

The addition of Lysine, L-arginine or Histidine further improves the activity of BAK. With as low as 0.5% w/v L-arginine in combination with 0.10M Tris buffer, the formulation passed DAB-9 with only 50 ppm BAK and 0.02% EDTA with a much better *P. aeruginosa* kill profile, as shown in FIG. 1. Thus, it is shown in accordance with the present invention that the combination of L-arginine and Tris lowers the amount of BAK necessary to preserve the resulting formulation.

Figure 2:
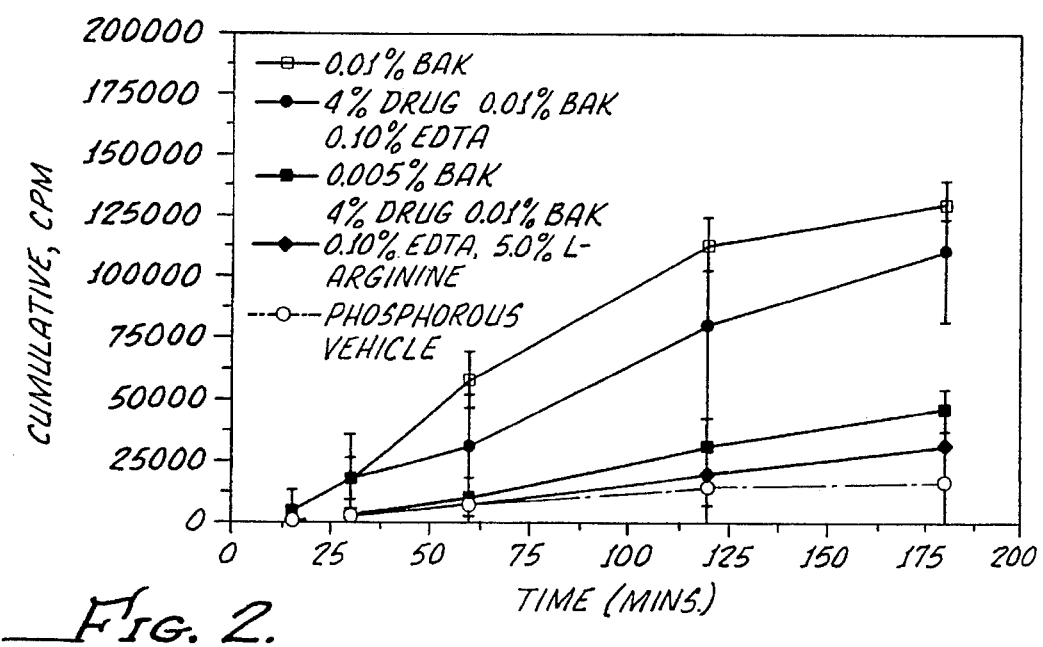
FIG. 2 is a comparison of inulin permeability (cytotoxicity) of formulations with and without L-arginine.

In the inulin permeation test, FIG. 2, the presence of L-arginine in the formulation significantly decreased the permeability (cytotoxicity) to tight junctions between the epithelial cells by approximately 4.5-fold in comparison to other formulations.

Thus, as shown in FIG. 2, formulations containing 100 ppm BAK, 0.1% EDTA, and 5% L-arginine have less permeability (less cytotoxicity) than the 50 ppm BAK control.

In accordance with the present invention, the addition of an amino acid, having a net positive charge at about neutral pH, such as Lysine, L-arginine, and Histidine, along with Tris, compete with and prevent BAK from complexing with an anionic drug such as Bufrolin. Thus, the amino acid and/or the Tris are effective in maintaining a stable and adequately preserved formulation. In addition, the presence of an amino acid having a net positive charge at 7.4 pH, such as L-arginine, greatly decreases the cytotoxicity of the formulation.

It should be noted that the effectiveness of the formulation is well within the 5 to 7.6 pH, generally accepted for ophthalmic formulations, with an ideal pH of 7.4 for comfort in use of the formulation. Also, while it is preferable to maintain the concentration of BAK below 100 ppm, such as—for example—25 ppm, 50 ppm, or 75 ppm, formulations may be effective with higher amounts of BAK corresponding to greater amounts of Tris or L-arginine of more than about 4%.

Although there has been hereinabove described a specific ophthalmic solution and method in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A formulation comprising:

a drug interactive with benzalkonium chloride; benzalkonium chloride active as a preservative; and L-arginine present in an amount sufficient to interfere with the interaction between the drug and benzalkonium chloride in order to maintain the preservative activity of the benzalkonium chloride.

2. The formulation according to claim 1 wherein the drug is selected from a group consisting essentially of Prostaglandins, Flurbiprofen, Keterolac Tromethamine, Cetirizine HCl and Indomethacin.

3. The ophthalmic formulation according to claim 1 wherein said drug comprises Bufrolin.

4. The ophthalmic formulation according to claim 3 wherein the drug comprises Bufrolin present in an amount up to about 4% w/v.

5. The formulation according to claim 1 wherein the L-arginine is present in an amount of between about 0.5% and about 5% w/v.

6. The formulation according to claim 5 wherein the benzalkonium chloride is present in an amount less than about 100 ppm.

7. A formulation comprising:

a drug having a negative charge at the pH of the formulation;

benzalkonium chloride present in a preservative effective amount; and

L-arginine present in an amount sufficient to enhance the preservative effectiveness of the benzalkonium chloride.

8. The ophthalmic formulation according to claim 7 wherein the drug comprises Bufrolin present in an amount up to about 4% w/v.

9. The ophthalmic formulation according to claim 8 wherein the L-arginine is present in an amount of between about 0.5% and about 5% w/v.

10. The formulation according to claim 8 wherein the benzalkonium chloride is present in an amount less than about 100 ppm.

11. A formulation comprising:

an anionic drug capable of forming an insoluble complex with benzalkonium chloride;

benzalkonium chloride present in a preservative effective amount; and

L-arginine present in an amount effective to reduce cytotoxicity of the formulation.

12. The formulation according to claim 11 wherein said drug comprises Bufrolin.

13. The formulation according to claim 11 wherein the drug comprises Bufrolin present in an amount up to about 4% w/v.

14. The formulation according to claim 13 wherein the L-arginine is present in an amount of between about 0.5% and about 5% w/v.

15. The formulation according to claim 14 wherein the benzalkonium chloride is present in an amount less than about 100 ppm.

16. A method for preserving a formulation comprising the step of combining a drug interactive with benzalkonium chloride with benzalkonium chloride active as a preservative and L-arginine and Tromethamine present in an amount sufficient to interfere with the interaction between the drug and benzalkonium chloride in order to maintain the preservative activity of the benzalkonium chloride.

17. The method according to claim 16 wherein the drug is selected from a group consisting essentially of Prostaglandins, Flurbiprofen, Keterolac Tromethamine, Cetirizine HCl and Indomethacin.

18. The method according to claim 17 wherein said drug comprises Bufrolin.

19. The method according to claim 17 wherein the drug comprises Bufrolin present in an amount up to about 4% w/v.

20. The method according to claim 16 wherein the L-arginine is combined in an amount of between about 0.5% and about 5% w/v.

21. The method according to claim 20 wherein the benzalkonium chloride is combined in an amount less than about 100 ppm.

22. The method according to claim 16 further comprising the step of combining Tromethamine in an amount sufficient to lower the amount of benzalkonium chloride necessary to preserve the combination.

23. The method according to claim 22 wherein the amount of Tromethamine combined is between about 0.3% and about 2% w/v.

* * * * *